(12) United States Patent
VanDine et al.

(10) Patent No.: US 8,614,101 B2
(45) Date of Patent: Dec. 24, 2013

(54) IN SITU LYSIS OF CELLS IN LATERAL FLOW IMMUNOASSAYS

(75) Inventors: Robert W. VanDine, Montoursville, PA (US); Uma Mahesh Babu, Bradenton, FL (US); Robert P. Sambursky, Bradenton, FL (US)

(73) Assignee: Rapid Pathogen Screening, Inc., Sarasota, FL (US)

( * ) Notice: Subject to any disclaimer, the term of this patent is extended or adjusted under 35 U.S.C. 154(b) by 742 days.

(21) Appl. No.: 12/502,662

(22) Filed: Jul. 14, 2009

(65) Prior Publication Data

US 2010/0015634 A1    Jan. 21, 2010

Related U.S. Application Data

(63) Continuation-in-part of application No. 12/469,207, filed on May 20, 2009, now abandoned, and a continuation-in-part of application No. 12/481,631, filed on Jun. 10, 2009, now Pat. No. 8,470,608.

(60) Provisional application No. 61/080,879, filed on Jul. 15, 2008, provisional application No. 61/098,935, filed on Sep. 22, 2008, provisional application No. 61/179,059, filed on May 18, 2009, provisional application No. 61/071,833, filed on May 20, 2008, provisional application No. 61/060,258, filed on Jun. 10, 2008.

(51) Int. Cl.
    *G01N 33/558* (2006.01)
(52) U.S. Cl.
    USPC ........ 436/514; 422/420; 422/425; 435/287.7; 435/287.9; 435/805; 435/810; 435/970; 435/973; 436/169; 436/177; 436/530; 436/810

(58) Field of Classification Search
    None
    See application file for complete search history.

(56) References Cited

U.S. PATENT DOCUMENTS 4,094,647 A * 6/1978 Deutsch et al. .................. 435/4
4,861,711 A * 8/1989 Friesen et al. ............... 435/7.92

(Continued)

FOREIGN PATENT DOCUMENTS

DE    19622503 C2    7/1998
EP     1489416 A1    3/2003

(Continued)

OTHER PUBLICATIONS

Extended European Search Report, European Patent Office, Feb. 10, 2012.

(Continued)

*Primary Examiner* — Chris L Chin
(74) *Attorney, Agent, or Firm* — Brown & Michaels, PC

(57) ABSTRACT

Devices and methods incorporate lysis agents into a point-of-care testing device. The sample is loaded, and then the sample travels until it encounters a lysis agent. The lysis agent is preferably pre-loaded onto the collection device. In a preferred embodiment, the initially lysis agent is localized between the sample application zone and the conjugate zone. The lysis agent is preferably soluble or miscible in the sample transport liquid, and the lysis agent is solubilized and activated upon contact with the sample transport liquid. The sample transport liquid then contains both lysis agent in solution or suspension and sample components in suspension. Any lysis-susceptible components in a sample, then being exposed in suspension to the lysis agent, are themselves lysed in situ. The running buffer then carries the analyte, including any lysis-freed components, to the detection zone.

10 Claims, 8 Drawing Sheets

(56) References Cited

U.S. PATENT DOCUMENTS

| | | | |
|---|---|---|---|
| 4,960,691 A * | 10/1990 | Gordon et al. | 435/6.12 |
| 5,120,643 A | 6/1992 | Ching et al. | |
| 5,496,562 A | 3/1996 | Burgoyne | |
| 5,607,863 A * | 3/1997 | Chandler | 436/518 |
| 5,637,469 A | 6/1997 | Wilding et al. | |
| 5,695,949 A | 12/1997 | Galen et al. | |
| 5,714,341 A | 2/1998 | Thieme et al. | |
| 5,756,126 A | 5/1998 | Burgoyne | |
| 5,807,527 A | 9/1998 | Burgoyne | |
| 5,824,268 A | 10/1998 | Bernstein et al. | |
| 5,869,345 A | 2/1999 | Chandler | |
| 5,939,252 A | 8/1999 | Lennon et al. | |
| 5,972,386 A | 10/1999 | Burgoyne | |
| 5,985,327 A | 11/1999 | Burgoyne | |
| 6,106,779 A | 8/2000 | Buechler et al. | |
| 6,350,578 B1 | 2/2002 | Stark et al. | |
| 6,358,752 B1 | 3/2002 | Durst et al. | |
| 6,368,876 B1 | 4/2002 | Huang et al. | |
| 6,514,773 B1 | 2/2003 | Klein et al. | |
| 6,875,619 B2 | 4/2005 | Blackburn | |
| 7,374,950 B2 | 5/2008 | Kang et al. | |
| 7,379,167 B2 | 5/2008 | Mawhirt et al. | |
| 7,393,697 B2 | 7/2008 | Charlton | |
| 7,425,302 B2 | 9/2008 | Piasio et al. | |
| 7,723,124 B2 | 5/2010 | Aberl et al. | |
| 7,939,342 B2 * | 5/2011 | Song et al. | 436/514 |
| 2003/0104506 A1 | 6/2003 | Durst et al. | |
| 2003/0186463 A1 | 10/2003 | Hudak et al. | |
| 2004/0110167 A1 | 6/2004 | Gerdes et al. | |
| 2004/0156037 A1 | 8/2004 | Mawhirt et al. | |
| 2004/0241779 A1 | 12/2004 | Piasio et al. | |
| 2005/0227223 A1 | 10/2005 | Miyawaki | |
| 2005/0239056 A1 | 10/2005 | Piasio et al. | |
| 2006/0160078 A1 | 7/2006 | Cardy et al. | |
| 2006/0240569 A1 | 10/2006 | Goldenbaum et al. | |
| 2007/0059682 A1 | 3/2007 | Aberl et al. | |
| 2007/0141564 A1 | 6/2007 | Aberl et al. | |
| 2007/0264629 A1 | 11/2007 | Holmes et al. | |
| 2008/0085525 A1 | 4/2008 | Van Herwijnen | |
| 2009/0011436 A1 | 1/2009 | Piasio et al. | |
| 2009/0232702 A1 | 9/2009 | Wu et al. | |
| 2010/0143891 A1 | 6/2010 | Aberl et al. | |
| 2010/0291536 A1 | 11/2010 | Viljoen et al. | |

FOREIGN PATENT DOCUMENTS

| | | | |
|---|---|---|---|
| JP | 2000502452 A | 2/2000 |
| JP | 2005017248 A | 1/2005 |
| WO | 9723781 A1 | 7/1997 |
| WO | 03073817 A2 | 9/2003 |
| WO | 2004076054 A2 | 9/2004 |
| WO | 2006115866 A1 | 11/2006 |
| WO | 2007070117 A1 | 6/2007 |
| WO | 2008014709 A1 | 2/2008 |
| WO | 2009044167 A1 | 4/2009 |

OTHER PUBLICATIONS

Uchio, et al., "Rapid Diagnosis of Adenoviral Conjunctivitis on Conjunctival Swabs by 10-Minute Immunochromatography," Opthalmology, vol. 104, No. 8, Aug. 1997, pp. 1294-1299.

Sambursky et al., "The RPS Adeno Detector for Diagnosing Adenoviral Conjunctivitis", Ophthalmology, vol. 113, No. 10, pp. 1758-1764 (Oct. 2006).

Sambursky, "510-K Summary of Safety and Effectiveness" (Sep. 14, 2005).

Udeh et al., "Cost Effectiveness of a Point-of-Care Test for Adenoviral Conjunctivitis", The American Journal of the Medical Sciences, vol. 336, No. 3, pp. 254-264 (Sep. 2008).

Barnard, et al., "Development of an Oligonucleotide-Based SNP Detection Method on Lateral Flow Strips Using Hexapet Tags," Point of Care, vol. 4, No. 3, pp. 108-118 (Sep. 2005).

"FTA Nucleic Acid Collection, Storage and Purification," Whatman website, http://whatman.com/products.aspx? PID=108 and http://www.whatman.com/FTANucleicAcidCollectionStorageandPurification.aspx.

Karle, et al., "Application of FTA-based Technology for Sample Collection, Transport, Purification, and Storage of PCR-ready Plant DNA" (Nov. 2003).

O'Mahony, et al., "Integration of Bacteria Capture via Filtration and in Situ Lysis for Recovery of Plasmid DNA under Industry-Compatible Conditions," Biotechnol. Prog. 2007, 23, pp. 895-903.

Berezovski, et al., "Cell lysis inside the capillary facilitated by transverse diffusion of laminar flow profiles (TDLFP)," Anal Bioanal Chem (2007) 387:91-96.

International Search Report and Written Opinion, International Application No. PCT/US2009/050653, Mar. 12, 2010.

Chieux, et al. "The MxA protein levels in whole blood lysates of patients with various viral infections". J Virol Methods. 1998;70:183-191.

\* cited by examiner

IN SITU LYSIS OF CELLS IN LATERAL FLOW IMMUNOASSAYS

REFERENCE TO RELATED APPLICATIONS

This application claims one or more inventions which were disclosed in Provisional Application No. 61/080,879, filed Jul. 15, 2008, entitled "LATERAL FLOW NUCLEIC ACID DETECTOR", Provisional Application No. 61/098,935, filed Sep. 22, 2008, entitled "IN SITU LYSIS OF CELLS IN LATERAL FLOW IMMUNOASSAYS", and Provisional Application No. 61/179,059, filed May 18, 2009, entitled "METHOD AND DEVICE FOR COMBINED DETECTION OF VIRAL AND BACTERIAL INFECTIONS". The benefit under 35 USC §119(e) of the U.S. provisional applications are hereby claimed, and the aforementioned applications are hereby incorporated herein by reference.

This application is also a continuation-in-part application of application Ser. No. 12/469,207, filed May 20, 2009, entitled "NANOPARTICLES IN DIAGNOSTIC TESTS", now abandoned, which claimed priority from Provisional Application No. 61/071,833, filed May 20, 2008, entitled "NANOPARTICLES IN DIAGNOSTIC TESTS" and application Ser. No. 12/481,631, filed Jun. 10, 2009, entitled "COMBINED VISUAL/FLUORESCENCE ANALYTE DETECTION TEST", now U.S. Pat. No. 8,470,608 which claimed priority from Provisional Application No. 61/060,258, filed Jun. 10, 2008, entitled "COMBINED VISUAL/FLUORESCENCE ANALYTE DETECTION TEST". The aforementioned applications are hereby incorporated herein by reference.

BACKGROUND OF THE INVENTION

1. Field of the Invention

The invention pertains to the field of lateral flow immunoassays. More particularly, the invention pertains to in situ lysis of samples in lateral flow immuonassays.

2. Description of Related Art

Lateral flow immunoassays combine the reagents and the process steps of more general immunoassays into an improved assay. This enables single-step, point-of care testing (POCT) and provides a sensitive and rapid means for detection of target molecules. Lateral flow immunoassays are available for a wide array of target analytes and can be designed for sandwich or competitive test formats. Generally high molecular weight analytes with several epitopes are analyzed in a sandwich format whereas small molecules representing only one epitope are detected by means of a competitive assay. The first lateral flow assays tested for human chorionic gonadotropin (hCG). Today commercially available tests monitor ovulation, detect infectious disease organisms, analyze drugs of abuse and measure other analytes important to human physiology. Products have also been introduced for veterinary testing, environmental testing, and product monitoring.

U.S. Pat. No. 5,714,341 discloses a lateral flow immunoassay for HIV specific antibodies in saliva samples. A saliva sample is diluted in a sample buffer, and a lateral flow immunoassay is dipped into the diluted saliva sample, again enabling point-of-care testing with rapid results.

German Patent DE19622503 discloses a lateral flow immunoassay for illegal narcotics in saliva and sweat.

There is a need for still simpler-to-use and more rapid lateral flow immunoassays suitable for time-sensitive and cost-sensitive clinical settings. This need is most acute in situations where the sample type and target analyte necessitate a sample preparation step. This may occur when an analyte is not readily presented within a sample and a separate lysis step is necessary to free the analyte for efficient presentation. Such an assay may need to directly test for analytes in human body fluids, including analytes which may be protected within complexes or behind cellular membranes.

As an example, fever is a common cause of childhood visits to urgent care centers for both family practice and pediatric offices. Most commonly, this relates to either a respiratory infection or gastroenteritis. The high incidence of fever in children and the precautions administration of unnecessary antibiotics is reason to develop a rapid screening test for biomarkers that distinguish viral from bacterial infections.

The efficiency and even the probability of success of a given immunoassay will depend on the initial presentation of any antigens to be detected. Antigens and other targets must be accessible to antibodies of an assay. Access can be impacted if most or all of the available antigen is masked in a complex or is inaccessible behind a cell membrane, e.g. in a cell's cytoplasm. In these situations, a viable and efficient assay may need to include a lysis step designed to make an antigen accessible, either by breaking up a complex to unmask components or by removing barriers such as a cell wall, a membrane of a cell or organelle, or a coat of a virus. However, such an added lysis step may complicate and delay an assay, even causing it to be too complex or time consuming for practical operation in a clinical setting.

In order to detect analytes protected within a complex of molecules or behind a membrane or other barrier, one approach in the immunoassay field is to lyse the complex or barrier and extract the analyte of interest prior to performing the immunoassay. When the barrier is a cell wall or cell membrane, the cells can be erythrocytes, leukocytes, epidermal, viral, fungal or bacterial, and they can be normal or malignant. Traditionally, a required lysis step is accomplished prior to and physically separate from the desired immunoassay, as a sample preparation step.

Practical operation in point-of care testing means that an assay needs to operate in such a manner as to report a result meeting point-of-care testing requirements including but not limited to timeliness, accuracy, sensitivity, specificity, and ease of use. Therefore, there is a need in the art for methods and devices that can circumvent the need for a separate lysis step prior to running a lateral flow immunoassay.

SUMMARY OF THE INVENTION

Instead of lysing cells prior to transferring a sample to a point-of-care testing device, the present invention includes devices and methods that incorporate lysis agents into a point-of-care testing device so that lysis does not need to be conducted as a separate step. The lysis step is performed on the test strip itself, as an integral part of the sample analysis device.

DETAILED DESCRIPTION OF THE INVENTION

Figure 1:
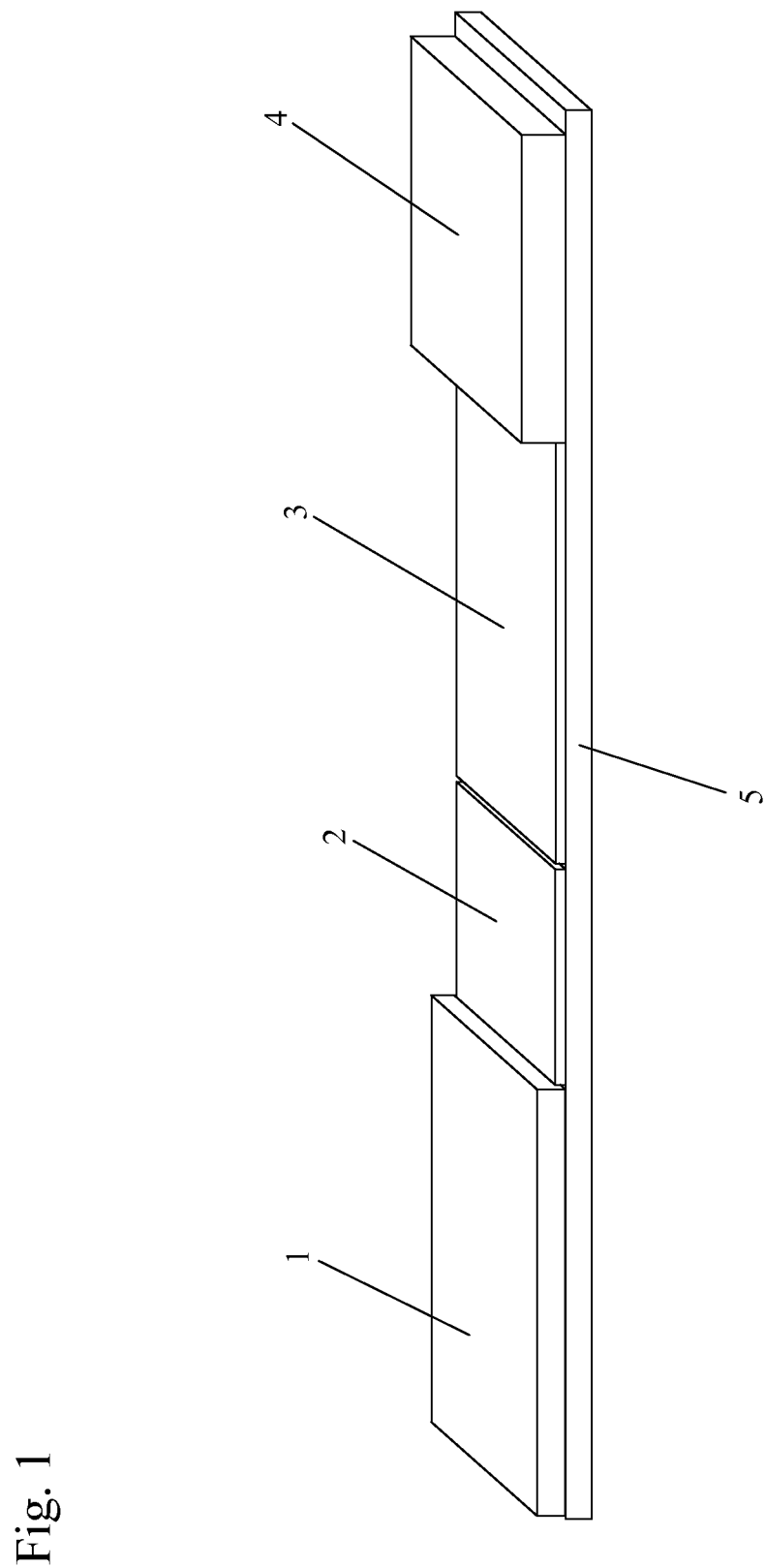
FIG. 1 shows a sample analysis device that may be used in embodiments of the present invention.

Instead of lysing cells "outside" of a point-of-care testing device, the present invention utilizes "in situ lysis". The term "in situ lysis", as used herein, describes techniques for incorporating lysis agents into a point-of-care testing device, such as a chromatography test strip or other lateral flow immunoassay device, so that the lysis operation is not conducted as a separate step.

In situ lysis offers distinct advantages over a separate lysis step. Some of these advantages are:
1. Higher efficiency. Cells that are lysed prior to being transferred onto the device would inherently lower the percentage of recovery. Thus, avoiding an additional transfer step promotes efficiency and sensitivity.
2. Higher stability. Many intra-cellular analytes are labile. By greatly reducing the time for interaction with an antibody and antigens in an in situ lysis set up, this lability can be overcome.
3. More rapid testing and results. In situ lysis eliminates the need of separate "outside" lysing steps, thus increasing the rapidity of test results in a point-of-care testing scenario.
4. Reducing interference. With a proper "blocking zone," one can block cell debris or cell bound materials from reaching an assay reaction area. Where an analyte of interest is intra-cellular and a protein associated with a cell wall and other cell debris needs to be blocked, and the assay antibody is protected, then a blocking zone downstream of the lysis agent and upstream of an assay readout may be used to decrease interference.

"In situ lysis" can also be applied to "breaking down of the complexes," whether they are immune complexes or bound materials of some kind. By lysing these complexes in situ, one can then measure the amount of analyte in the complexes.

In a preferred embodiment, the sample analysis device includes a chromatographic test strip, e.g. a lateral flow or flow through test strip. The test strip includes a sample application zone, a lysis zone, a conjugate zone, and a detection zone. Preferably, the test strip also optionally includes a waste zone, a control zone, a carrier backing, a housing and an opening in the housing for read out of the result. Any combinations of some or all of these elements may be included in the test strip. Sample analysis in the detection zone may be carried out by standard means, e.g. by an immunological, biochemical or enzymatic detection method. Preferably, the detection method includes the use of antibodies, nucleic acids, ligands/receptors or nanoparticles capable of specifically binding the targets, e.g. pathogens to be tested and subsequent visualization of the bound entity, e.g. by enzymatic detection or by means of direct labeling groups, such as visible or colored particles, dyes, magnetic particles, fluorescent or phosphorescent particles, chemiluminescent particles, radioisotopic ligands, enzymes, peptides, amino acids, colloidal particles, or beads, as is well known in the art.

Detection of the marker may be achieved in the detection zone. The binding molecule immobilizes the labeled complex or the labeled marker-analogue by immune reaction or other reaction in the detection zone, thus building up a visible test line in the detection zone during the process. Preferably, the label is an optically detectable label. Forming a complex at the test line concentrates and immobilizes the label and the test line becomes visible to the naked eye, indicating a positive test result. Particularly preferred are direct labels, and more particularly gold labels which can be best recognized by the naked eye. Additionally, an electronic read out device (e.g. on the basis of a photometrical, acoustic, impedimetrical, potentiometric and/or amperometric transducer) can be used to obtain more precise results and a semi-quantification of the analyte. Other labels may be latex, fluorophores, or phosphorophores.

Furthermore, this invention includes a device and test kit for the performance of the described method.

In some preferred embodiments, the specific binding partners for the analytes in the sample are monoclonal, polyclonal, single domain or recombinant antibodies, or fragments of antibodies capable of binding to a pathogen. Alternatively, the specific binding partners may also be antigens capable of binding to antibodies against a pathogen or an allergen. Other types of binding partners include, but are not limited to, bioorganic macromolecules like aptamers or ligands/receptors, nanoparticles, or nucleic acids.

The visual label may be any label visible to the naked eye, including, but not limited to, colored particles such as colloidal gold, dyed latex beads, selenium, or carbon. In some embodiments, the visual tags are also coated with fluorescing elements. In some embodiments, the fluorescing element is a fluorescing dye. Alternatively, a mixture of preferably colorless fluorescing latex bead conjugates are mixed with colloidal gold (a visible spectrum) conjugates, or conjugates producing a visible read test line, in lateral flow immunoassays to enhance sensitivity of the assay and to aid in visually reading true positives and true negatives. In embodiments where nanoparticles are used, the nanoparticles that may be used include, but are not limited to, selenium, carbon, and colloidal gold.

Preferred targets include, but are not limited to, proteins, glycoproteins, proteoglycans, nucleic acids, and lipoproteins. Other preferred targets include, but are not limited to, pathogens, low-molecular-weight compounds, and/or allergy-associated components. The pathogens are preferably selected from viruses, microorganisms, e.g. bacteria, and parasites, e.g. amoebae or nematodes. The allergy-associated components are preferably selected from allergens and anti-allergic components.

In some preferred embodiments, the sample is a sample of body fluid. In these embodiments, the sample of body fluid is preferably taken from a body surface selected from mucosal membrane fluids (preferably of the oral, nasal, vaginal, and ocular cavities), blood, urine, tears, cerebrospinal fluid, secretions from glands and secretions from lesions or blisters, e.g. lesions or blisters on the skin. More preferably, the sample is selected from oral, nasal, ocular, genital and rectal fluid, secretions from skin lesions or blisters, CSF (cerebral spinal fluid), and exudates. In some embodiments, the body fluid samples are preferably fluids that do not flow once collected.

Lateral flow devices are known, and are described in, e.g., U.S. Published Patent Application Nos. 2005/0175992 and 2007/0059682. The contents of both of these applications are incorporated herein by reference. Other lateral flow devices known in the art could alternatively be used with the systems and methods of the present invention.

U.S. Published Patent Application No. 2007/0059682, discloses detecting an analyte and a sample which can also contain one or more interfering substances. This publication teaches separating the analyte from the interfering substances by capturing the interfering substances on the chromatographic carrier, and detecting the analyte on the carrier separated from the interfering substances.

U.S. Published Patent Application No. 2005/0175992 discloses a method for detecting targets, such as pathogens and/or allergy-associated components, in a human body fluid where the body fluid sample is collected by a collection device, such as a swab member. The samples are transferred from the swab member to a sample analysis device, on which an analysis of the targets can occur by immunochemical or enzymatic means. The test result is capable of being displayed within a very short period of time and can be directly read out by the user. This enables point-of-care testing with results available during a patient visit. The inventions disclosed in this copending application are particularly advantageous for the diagnosis of conjunctivitis.

The chromatographic test strip shown in FIGS. 1 through 4 includes a plurality of different strip materials. The device preferably includes an absorbent pad (1), an application zone (2), a detection zone (3), and a waste zone (4). The strip materials are arranged on an adhesive plastic backing (5). The absorbent pad (1) is provided in this example for adding an elution medium in order to facilitate the transfer of the sample to the detection zone (3). US Published Patent Application No. 2007/0059682, describes methods to increase specificity of lateral flow immunoassays. These methods could also be used in combination with the embodiments described herein.

Figure 2:
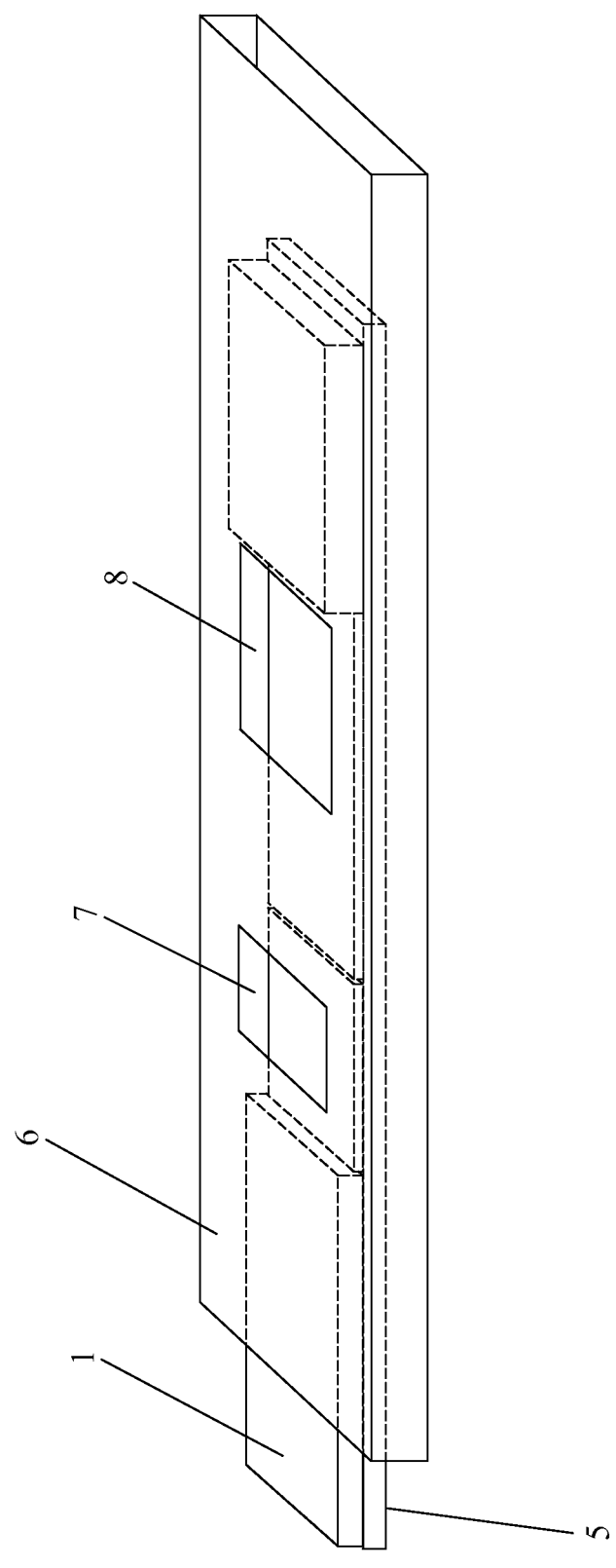
FIG. 2 shows a housing containing the strip of FIG. 1.
Figure 3:
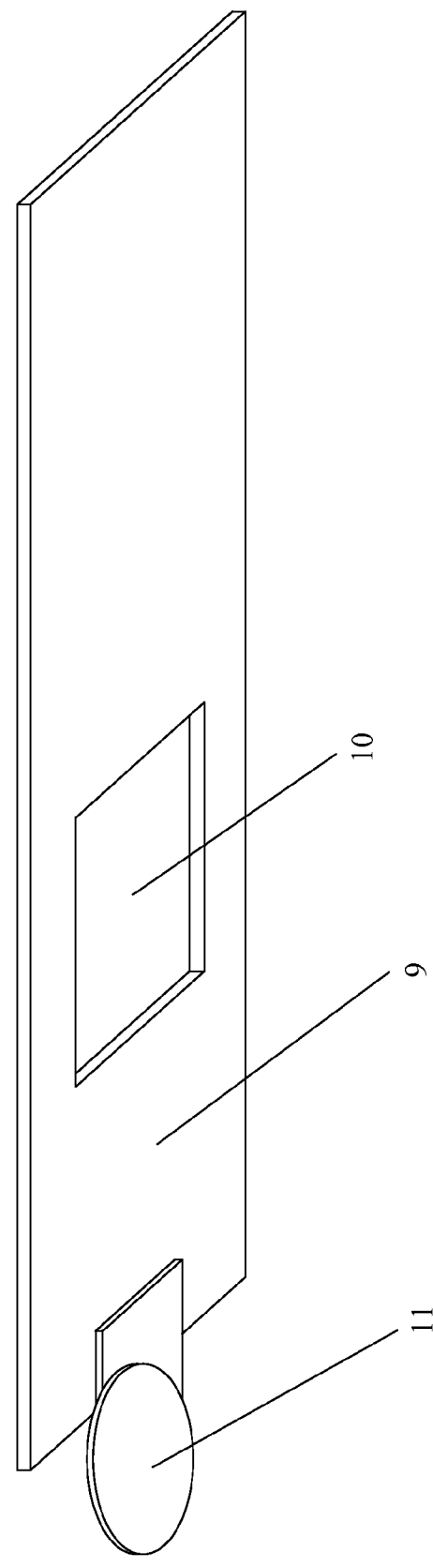
FIG. 3 shows a collection device for collecting a sample.
Figure 4:
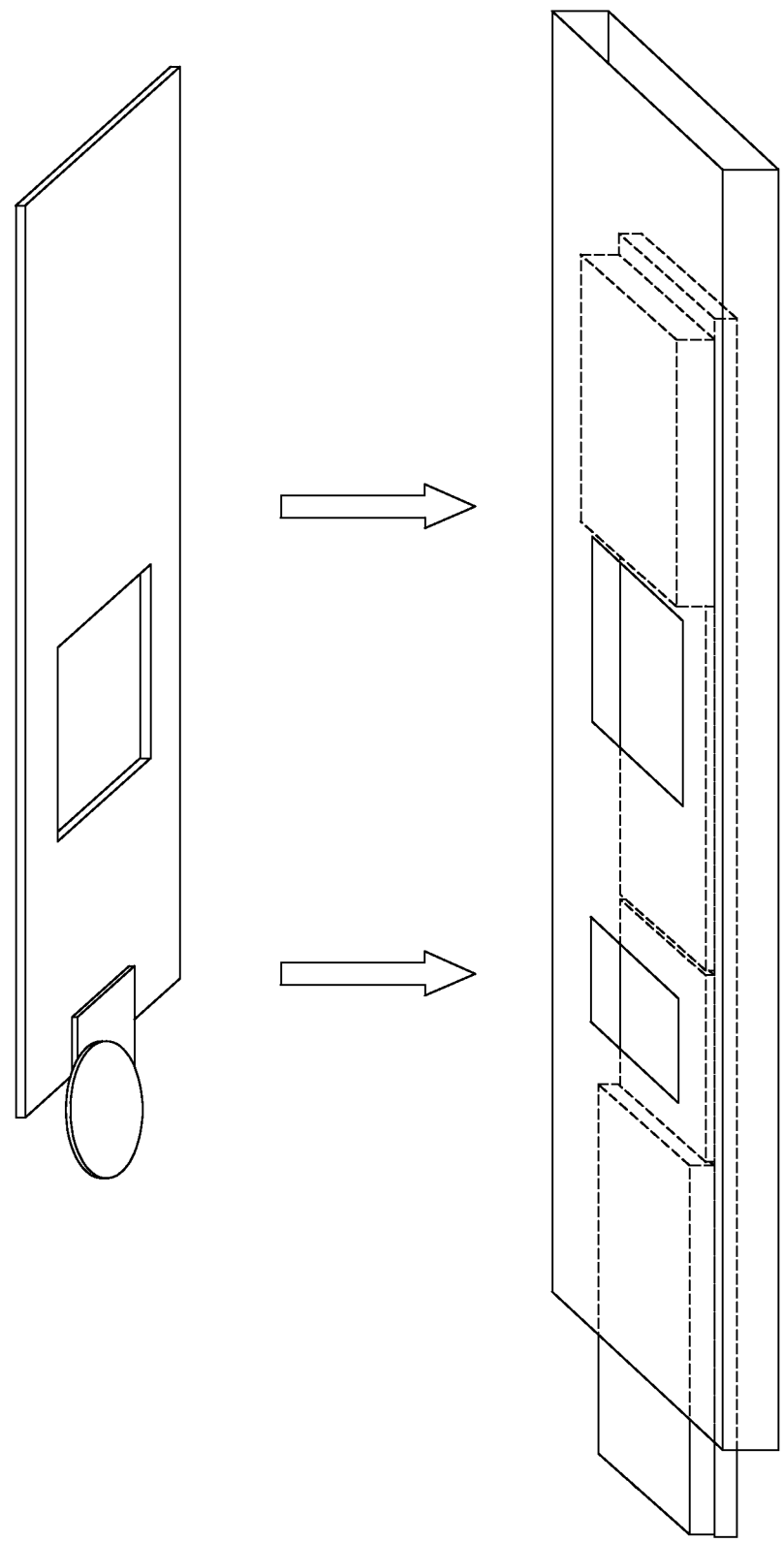
FIG. 4 shows a test kit including the sample analysis device of FIGS. 1 and 2 and the collection device of FIG. 3.

FIG. 2 shows a housing (6), which is preferably plastic, containing the strip as shown in FIG. 1. A sample application window (7) brings a collection device into contact with the strip. The test result is displayed in the read out window (8). FIG. 3 shows the collection device for collecting a sample. In one example, the collection device is a swab member. The collection device includes a body (9), which is preferably plastic, with a sample collection material (11) fixed on it and an opening (10) corresponding to a read out window when the collection device is operatively in contact with a test strip. FIG. 4 shows a test kit, which includes the sample analysis device of FIGS. 1 and 2 and the collection device of FIG. 3.

The methods and devices of the present invention incorporate a lysis zone including at least one lysis agent as part of a lateral flow immunoassay test strip, such as those shown in FIGS. 1 through 4, or other lateral flow immunoassay devices known in the art, in order to lyse the sample material in situ.

The present invention is suitable for various methods for loading the sample. The assay will either be started directly when sample is transferred in a sufficient volume of liquid, such as a body fluid, or the process may require that a sample be added to or eluted by a sample transport liquid (e.g. tap water or a buffer solution). In one preferred embodiment, a sample which has been collected, such as by a swab, is transferred directly onto the sample application zone of a test strip. In this embodiment, a sample transport liquid is then added to the test strip. In another preferred embodiment, a liquid sample is deposited directly onto the sample application zone of a test strip. In this embodiment, the liquid sample itself, if of sufficient volume, becomes the transport liquid. If the volume of the liquid sample is insufficient, then a sample transport liquid is additionally added. In yet another preferred embodiment, a liquid sample is pre-mixed with the sample transport liquid and then both are applied to the test strip together.

Following sample loading, sample traveling with the transport liquid will encounter the lysis agent. The lysis agent will have been pre-loaded onto the test strip and is eluted by the transport liquid. In some preferred embodiments the lysis agent has been dried into the test strip. Alternatively, the lysis agent may be pre-dried by freeze drying or lyophilizing and then pre-loaded into the test strip. In other embodiments, the lysis agent may be absorbed, adsorbed, embedded or trapped on the test strip. In a preferred embodiment, the lysis agent is localized between the sample application zone and the conjugate zone. The lysis agent is preferably soluble or miscible in the sample transport liquid, and the lysis agent is solubilized and activated upon contact with the sample transport liquid. The sample transport liquid then contains both lysis agent in solution or suspension and sample components in suspension. Any lysis-susceptible components in the sample, then being exposed in suspension to the lysis agent, are themselves lysed in situ. The running buffer then carries the analyte, including any lysis-freed components, through the conjugate zone and to the detection zone.

The location where the lysis agent is pre-loaded can be varied as needed. In order to maximize the time that the sample has to interact with the lysis agent as well as to minimize the amount of lysis agent reaching the detection zone, the dried, absorbed, adsorbed, embedded, or trapped lysis agent may be located in or just downstream of the sample application zone. Or, in order to minimize the distance in which the lysed product must travel before reaching the conjugate zone, the lysis agent may be located closer to the conjugate zone.

The concentration of lysis agent pre-loaded onto a test strip is preferably between 0.001% and 5% weight/volume. The volume to be pre-loaded depends on where the lysis agent is pre-loaded. Appropriate ranges are 1 to 10 microliters when pre-loaded into the sample collector fleece (the sample application zone) or 5 to 50 microliters when pre-loaded into the absorbent pad or into other locations within the test strip. Ideally, the amount pre-loaded should be approximately 3 microliters pre-loaded into the sample collector fleece or approximately 10 microliters pre-loaded into the absorbent pad or into other locations within the test strip.

Selection of a specific lysing environment and agent will depend on the analyte and the assay. pH and ionic strength are key to the lysing environment. As to pH established by the lysis agent, a pH below 4.0 tends to precipitate materials, especially proteins. Higher pH, above approximately 10.0, tends to lyse materials such as proteins and cells walls. Therefore, a pH of approximately 10.0 or above is preferable for many applications. Alternatively, lower pH may be preferred for nucleic acid targets.

As to ionic strength established by the lysis agent, both high and low ionic strength may be used to lyse. For example, a lower ionic strength (hypotonic) tends to break up erythrocytes. Water by itself can lyse erythrocytes. Higher ionic strength environments may be used to rupture certain cell walls and membranes.

As to specific lysis agents, they may be grouped and selected based on their properties: salts, amphoteric and cationic agents, ionic and non-ionic detergents. The salt, Ammonium Chloride (NH₄Cl), lyses erythrocytes. Other salts, including, but not limited to, high concentrations of Sodium Chloride (NaCl) and Potassium Chloride (KCl), may rupture certain cell walls and membranes. Other lysis agents are amphoteric agents including, but not limited to, Lyso PC, CHAPS, and Zwittergent. Alternatively, cationic agents including, but not limited to, C16 TAB and Benzalkonium Chloride may be used as a lysis agent. Both ionic and non-ionic detergents are often used to break or lyse the cell wall or cell membrane components such as lipoproteins and glycoproteins. Common ionic detergents include, but are not limited to, SDS, Cholate, and Deoxycholate. Ionic detergents are good solubilizing agents. Antibodies retain their activity in 0.1% SDS or less. Common non-ionic detergents include, but are not limited to, Octylglucoside, Digitonin, C12E8, Lubrol, Triton X-100, Noniodet P-40, Tween 20, and Tween 80. Non-ionic and mild ionic detergents are weaker denaturants and often are used to solubilize membrane proteins such as viral surface proteins. Additional lysis agents include, but are not limited to, urea and enzymes. Combinations of different lysis agents may be used to optimize the lysing environment.

Surfactants are generally wetting agents and lower the surface tension of a liquid. This then allows easier spreading by lowering the interfacial tension between liquids. So, surfactants can interfere with the natural binding of antigen and antibody or ligand and receptors. The concentrations are, therefore, experimentally chosen for each class of lysis agent. Once lysis occurs, it is important that the desired binding reactions not be hindered. Generally, 0.001% lysis agent concentration is considered the lower limit, and the upper limit is approximately 1%. There is an additive or synergistic effect when combinations of lysis agents are used. This expands the working range of concentration to run from approximately 0.001% to 1%. Finally, some undesirable non-specific binding may be prevented at a Tween 20 concentration of 5%. In all cases, the total amount of lysis agent pre-loaded onto all locations of an individual test strip must be sufficient to lyse barriers to immunodetection, permitting practical operation of the test strip.

The lysis agent itself should not interfere with any other assay detector or indicator agents and thus does not interfere with any other assay interactions and reactions to such an extent as to prevent practical operation of the assay. A lysis agent should have sufficient shelf life to allow manufacture, distribution and storage before use of a test strip in point-of-care testing.

In a preferred embodiment of the present invention, the lateral flow immunoassay device of the present invention includes a sample-transporting liquid, which can be a buffer, and a chromatography test strip containing one or several fleece materials or membranes with capillary properties through which sample flows. In a device and method of the invention, it is unnecessary to lyse the cells in the sample prior to applying it to the test strip.

In a preferred embodiment, as shown in FIGS. 5A through 5D, the sample is applied to the application zone (201) on a chromatography test strip (200). The sample passes a lysis zone (250), where a lysis agent will have preferably been pre-loaded onto the test strip and is eluted by the transport liquid. The lysis agent lyses any lysis-susceptible components in the sample in situ.

The chromatographic test strip contains a sample application zone (201), a lysis zone (250) containing a lysis agent, and a conjugate zone (260) containing at least one labeled binding partner that is eluted by and then able to migrate with a sample transport liquid (e.g. a buffer solution). The labeled binding partner is capable of specifically binding to an analyte of interest to form a conjugate which in turn is capable of specifically binding to another specific reagent or binding partner in the detection zone. Although not shown in these Figures, an absorbent pad, similar to the absorbent pad (1) shown in FIG. 1, as well as other known lateral flow immunoassay components including, but not limited to, a waste zone, a carrier backing, a housing and an opening in the housing for result read out may optionally also be a component of the test strip (200) in this embodiment.

In a preferred embodiment, the lysis agent is localized in the lysis zone (250) between the sample application zone (201) and the conjugate zone (260). The lysis agent is preferably soluble or miscible in the sample transport liquid, and the lysis agent is solubilized and activated upon contact with the sample transport liquid. The sample transport liquid then contains both lysis agent in solution or suspension and sample components in suspension. Any lysis-susceptible components in a sample, then being exposed in suspension to the lysis agent, are themselves lysed in situ. The running buffer then carries the analyte, including any lysis-freed components, to the detection zone (205).

Figure 5A:
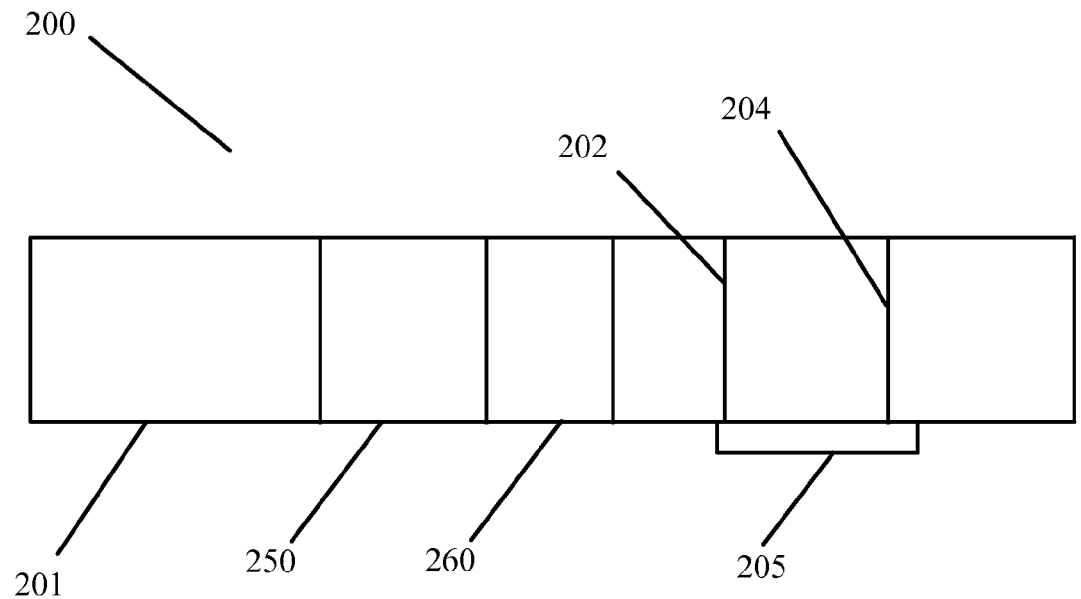
FIG. 5A shows a sample analysis device including a lysis zone located between a sample application zone and a conjugate zone in an embodiment of the present invention.
Figure 5B:
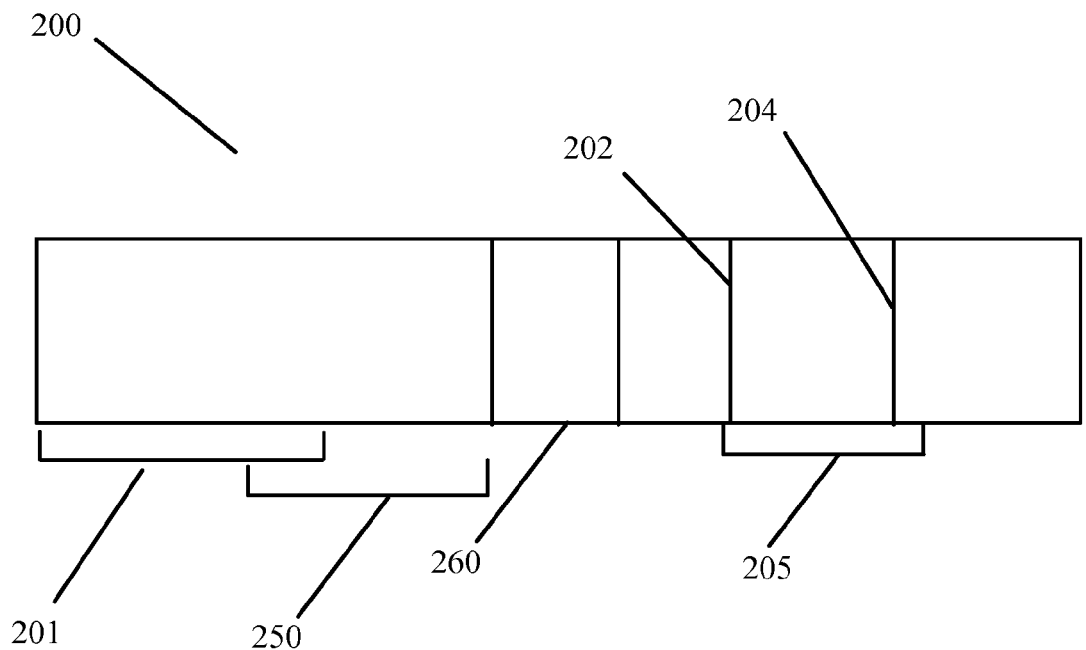
FIG. 5B shows a sample analysis device including a lysis zone overlapping a sample application zone in an embodiment of the present invention.
Figure 5C:
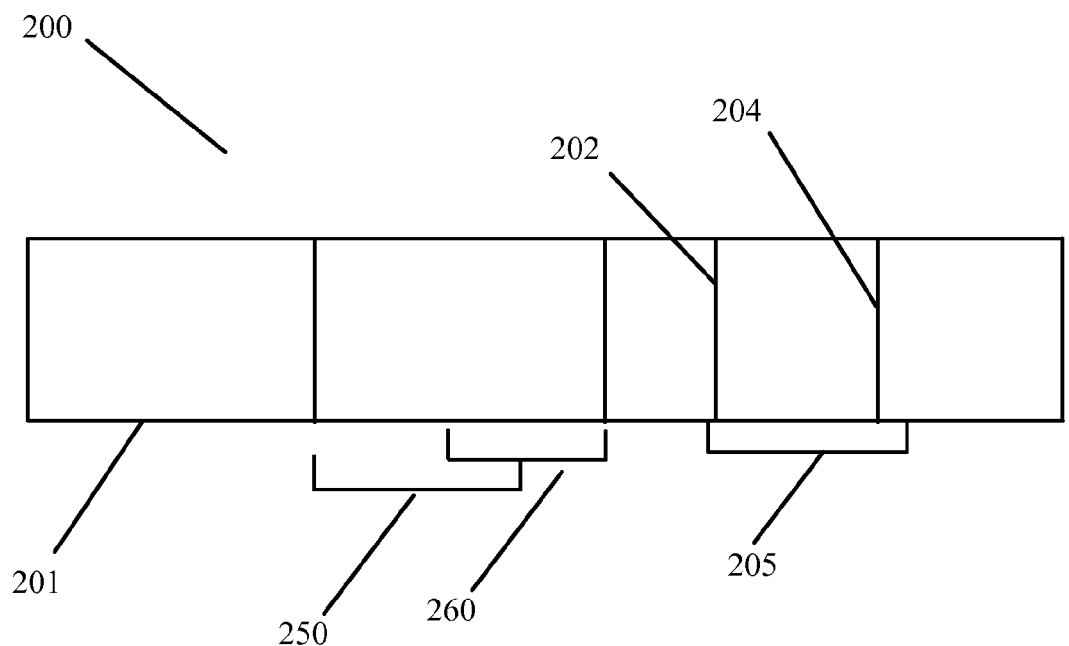
FIG. 5C shows a sample analysis device including a lysis zone overlapping a conjugate zone in an embodiment of the present invention.
Figure 5D:
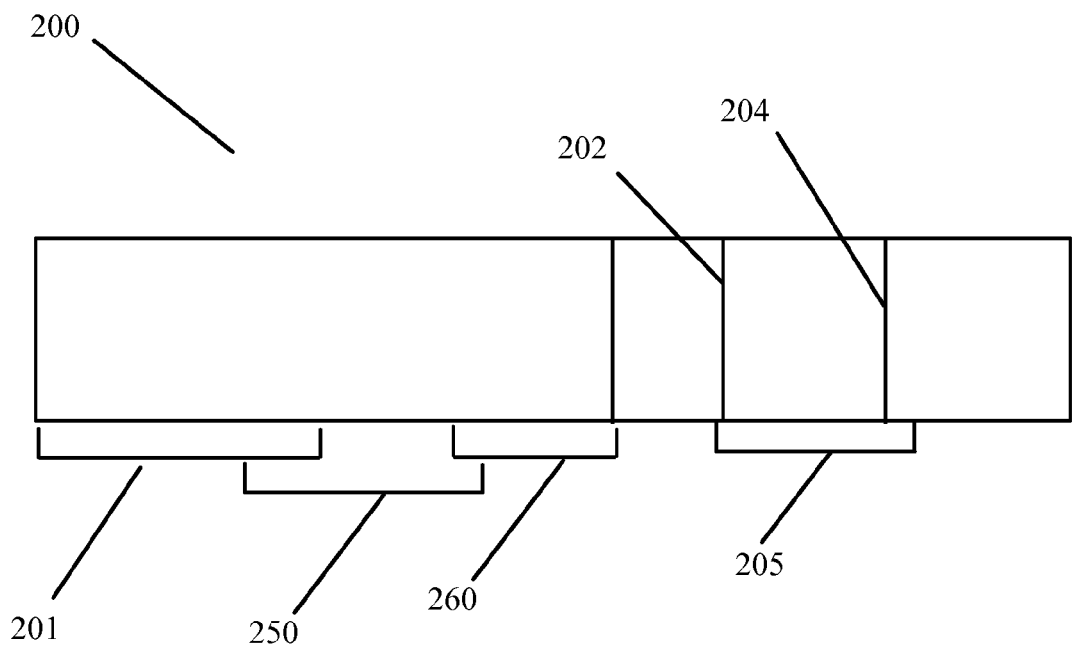
FIG. 5D shows a sample analysis device including a lysis zone overlapping a sample application zone and a conjugate zone in an embodiment of the present invention.
Figure 6A:
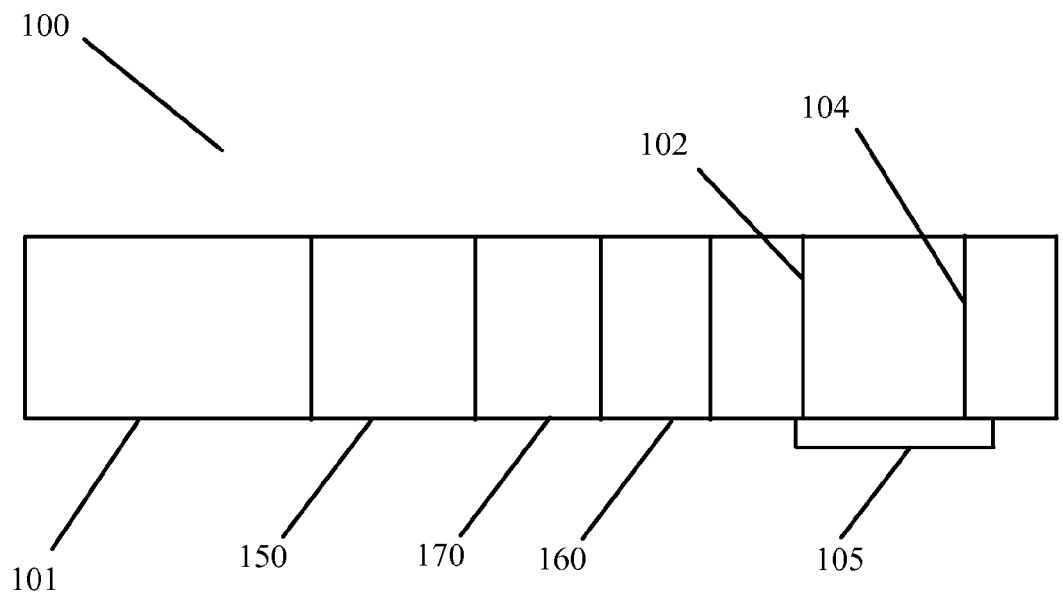
FIG. 6A shows a sample analysis device including a blocking zone between a sample application zone and a conjugate zone in an embodiment of the present invention.
Figure 6B:
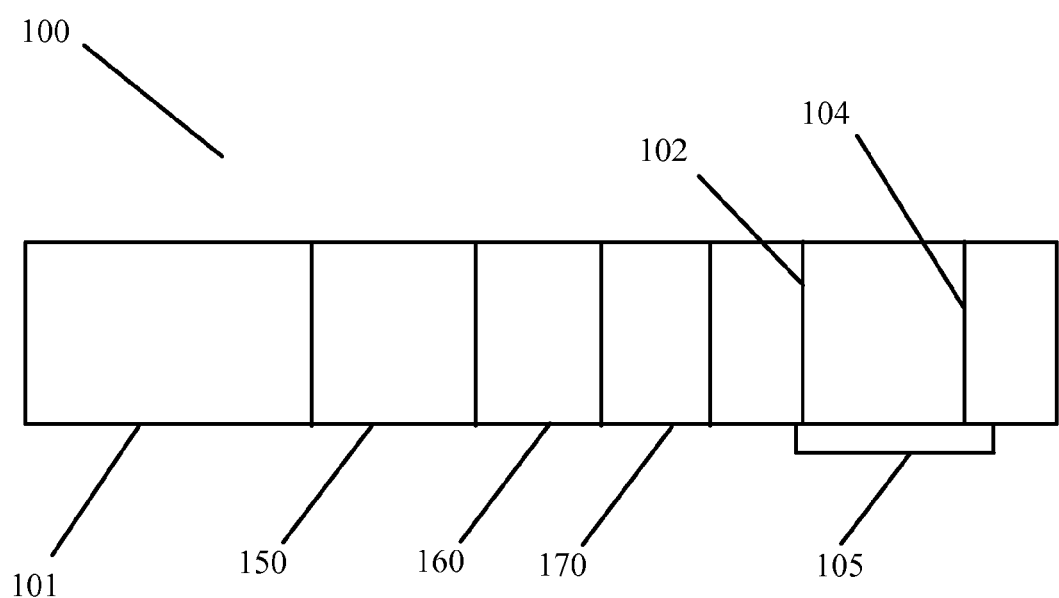
FIG. 6B shows a sample analysis device including a blocking zone between a sample application zone and a detection zone in another embodiment of the present invention.
Figure 6C:
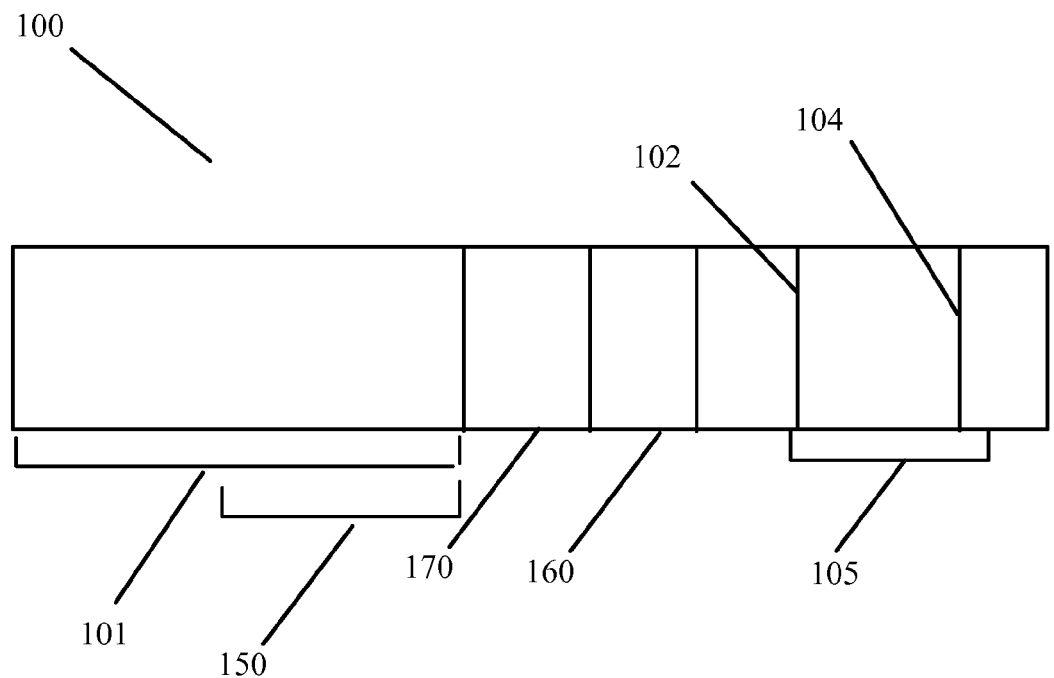
FIG. 6C shows a sample analysis device including a blocking zone between a sample application zone and a conjugate zone in another embodiment of the present invention.
Figure 6D:
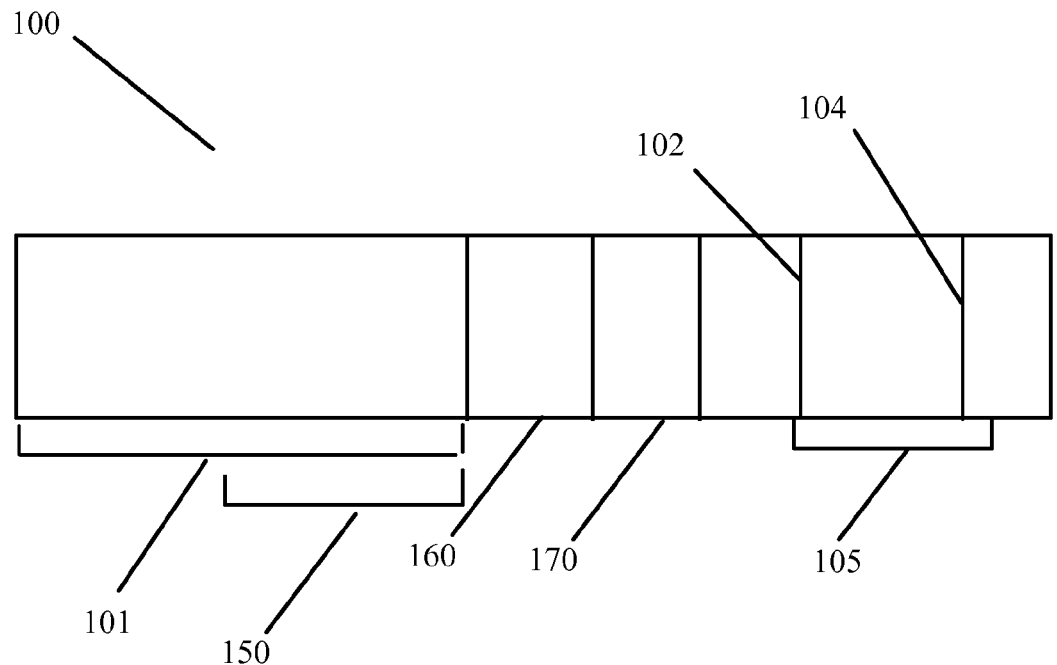
FIG. 6D shows a sample analysis device including a blocking zone between a sample application zone and a detection zone in another embodiment of the present invention

The lysis zone (250) is preferably located between the sample application zone (201) and the conjugate zone (260), as shown in FIG. 5A. In other embodiments, the lysis zone (250) overlaps the sample application zone (201), the conjugate zone (260) or both the sample application zone (201) and the conjugate zone (260) as shown in FIGS. 5B, 5C, and 5D, respectively. Note that the figures are schematic, and are not drawn to scale. The amount of overlap between the different zones (as shown in FIGS. 5B through 5D) may be highly variable.

The test strip (200) also includes a detection zone (205) containing a first section for detection of a first analyte, e.g. a test line (202), including an immobilized specific binding partner, complimentary to the conjugate formed in and arriving from the conjugate zone (260). Thus, at the test line (202), detection zone binding partners trap the labeled binding partners from the conjugate zone (260) along with their bound analytes. This localization of the analytes with their labeled binding partners gives rise to an indication at the test line (202). At the test line (202), the presence of an analyte is determined by qualitative and/or quantitative readout of the test line (202) indication resulting from the accumulation of labeled binding partners. Optionally, the detection zone (205) may contain further test lines to detect other analytes, as well as a control line (204). The control line (204) indicates that the labeled specific binding partner traveled through the length of the assay, even though it may not have bound any analyte, thus confirming proper operation of the assay. As shown in FIGS. 5A through 5D, the control zone (204) is preferably downstream of the test zone (202). However, in other embodiments, the control zone (204) may be located upstream of the test zone (202).

In a preferred embodiment, the control line (204) includes an antibody or other recombinant protein which binds to a component of the elution medium or other composition being used in the test. In embodiments where nucleic acids are the targets, the control line (204) preferably includes a nucleic acid complementary to the labeled nucleic acid being used as a binding partner for the target nucleic acid.

Although only one test line is shown in the figures, multiple test lines are within the spirit of the invention. In some embodiments where there are multiple targets, the presence of each target preferably corresponds to a separate test line (202). In other embodiments where there are multiple targets, the presence of multiple targets may be indicated on the same test line such that the presence of more than one target has different characteristics than the presence of a single target. For example, the presence of multiple targets on the same test line may be visually indicated by a different color than the presence of each of the targets alone.

In other embodiments, it is possible to have one or more mild lysis agents in the running buffer itself. In these embodiments, there is no adverse effect on the conjugate zone which will be downstream and the sample can either be upstream or downstream of the conjugate zone. A lysing enzyme in the running buffer can "target" its substrate and cut it to open up the cell wall. As an example, penicillin can excise or "punch a hole" in a susceptible bacteria. In other embodiments, when the lysis agent is applied to the sample collection material (11) (see FIG. 3), then the conjugate zone may be upstream of the sample application zone.

In another preferred embodiment, a barrier may be disposed in a "blocking zone" between the sample application zone and either the conjugate zone or the detection zone, preferably before the conjugate zone. In this case, the lysis agent is pre-loaded in the sample application zone or between the sample application zone and the barrier. Thus, lysis occurs before the sample reaches the barrier, and the barrier serves to slow or arrest those lysed materials effectively larger than the porosity of the barrier while permitting effectively smaller materials to pass more easily. Thus, the barrier provides a filtering effect and reduces interference with binding interactions in the conjugate and detection zones. Selection of a specific barrier material depends on the analyte and the assay.

A blocking zone barrier may be physical or biological. Examples of physical barriers include glass fiber matrices which inherently bind or trap erythrocytes and their cellular debris. Other physical matrices may be "sieve-type" matrices, as in a filtering system, where the small pore size blocks passage of cells but does allow passage of biomarkers.

In contrast, biological barriers are immobilized biological materials that specifically bind to ligands or receptors on a cell surface, preventing the cells from flowing further. Examples include antibodies, recombinant proteins, specific lectins, and receptors/ligands. Biological materials may also be combined into physical barriers such as glass fiber membranes.

FIGS. 6A through 6D show a barrier disposed in a "blocking zone" (170) between the sample application zone (101) and either the conjugate zone (160) (FIGS. 6A and 6C) or the detection zone (105) (FIGS. 6B and 6D) of the test strip (100). In either case, the lysis zone (150) either overlaps with the sample application zone (101) such that the lysis agent is pre-loaded in the sample application zone (101) (see FIGS. 6C and 6D) or the lysis zone (150) is located between the sample application zone (101) and the barrier in the blocking zone (170) such that the lysis agent is pre-loaded between the sample application zone (101) and the blocking zone (170) (see FIGS. 6A and 6B). Thus, lysis occurs before the sample reaches the blocking zone (170), and the barrier in the blocking zone (170) serves to slow or arrest those lysed materials effectively larger than the porosity of the barrier while permitting effectively smaller materials to pass more easily. Thus, the barrier provides a filtering effect and reduces interference with binding interactions in the conjugate (160) and detection zones (105). Selection of a specific barrier material depends on the analyte and the assay. Similar to FIGS. 5A through 5D, the detection zone (105) includes at least one test zone (102) and a control zone (104).

The analytical tests discussed herein preferably permit a result while the patient is still being examined by the practitioner. The results of the tests are preferably determined within 20 minutes of transferring the sample to the device. In a preferred embodiment, the test result is obtained in 10 minutes or less after applying the sample to the device, and it is preferably read at approximately 10 minutes. In samples that are highly positive, a readout of the test zone (preferably a test line) is visible within approximately 1-5 minutes.

In some embodiments, the devices and methods of the present invention detect nucleic acids in a sample without the use of an amplification step for the target nucleic acid. In some embodiments, the detected nucleic acids are also quantified. The lateral flow detector may be used to detect a target nucleic acid sequence associated with any target virus, bacterium, fungus, or other pathogen, any genetic deficiency, or any other target nucleic acid in a sample. The target nucleic acid may be any nucleic acid including, but not limited to, DNA, an oligonucleotide, messenger RNA, or any other type of RNA. The assay is preferably run within a matter of minutes to a few hours after the sample is obtained, but the assay may be run at a later time such as at least 24 hours after obtaining the sample. The flow of the transport liquid in the detector may be gravity-dependent or as a result of capillary action or surface tension. The transport liquid may be applied by dipping the test strip in the transport liquid or the transport liquid may be contained in a test housing for the test strip.

A lateral flow nucleic acid detector in these embodiments may be uniplanar with a single sheet on a test strip for the detection zone. Alternatively, the detector may be multiplanar with multiple detection zones on multiple sheets in fluid communication for simultaneous assays for the same or different target nucleic acids from the same or different samples.

A sample for testing in these embodiments may be any sample expected to potentially include a target nucleic acid including, but not limited to, saliva, tears, cerebral spinal fluid, skin lesions, vaginal fluid, penile fluid, mucus, tissue, blood, urine, an environmental water sample, and a soil sample. In most cases, it is preferable to add a denaturant or lysis agent in situ to the sample in order to make the nucleic acids in the sample accessible to the first and second complexes. The denaturant or lysis agent is preferably pre-loaded onto a zone of the test strip so that the sample may be applied directly to the test strip without a step of adding denaturant or lysis agent. The denaturant or lysis agent is pre-loaded onto the test strip in a location so that it frees the nucleic acids prior to the sample reaching the first complex on the test strip. The denaturant or lysis agent is preferably soluble or miscible in the transport liquid and located in the sample application zone or between the sample application zone and the zone where the first complex is pre-loaded.

In some embodiments, the sensitivity of visually read lateral flow immunoassay tests is enhanced by adding a small quantity of fluorescing dye or fluorescing latex bead conjugates to the initial conjugate material. When the visible spectrum test line is visibly present, the test result is observed and recorded. However, in the case of weak positives that do not give rise to a distinct visual test line, a light of an appropriate spectrum, such as a UV spectrum, is cast on the test line to excite and fluoresce the fluorescing latex beads which are bound in the test line to enhance the visible color at the test line.

In some embodiments, the present invention provides a lateral flow assay that uses the lysis zone to help differentiate viral and bacterial infections. One situation where a lysis agent improves assay efficiency is in assaying for the presence of Human MxA, a 78 kDa protein which accumulates in the cytoplasm as a response to viral infection. The presence of this protein can help to distinguish between bacterial and viral infection in febrile children. In situ lysis using a combination of 1% to 6% weight/volume CHAPS and 0.5% to 2% weight/volume NP40 as the lysis agent improves detection of MxA in fresh or frozen whole blood.

A combined point of care diagnostic device tests markers for both viral and bacterial infection, and can effectively assist in the rapid differentiation of viral and bacterial infections, for example at the outpatient office or during an urgent care visit. This ability can dramatically reduce health care costs by limiting misdiagnosis and the subsequent overuse of antibiotics. Such a practice may limit antibiotic allergies, adverse events, and antibiotic resistance. The rapid result obtained from the test also permits a result while the patient is still being examined by the practitioner.

In one preferred embodiment, the marker for viral infection is MxA and the marker for bacterial infection is C-reactive protein (CRP). High MxA protein levels are strongly correlated with systemic viral infection and increased CRP is more associated with bacterial infections. The present invention includes a rapid infectious screening test for identifying MxA and CRP in samples. MxA is present in leukocytes (white blood cells). Therefore, the sample can be taken anywhere leukocytes are available, for example in a peripheral blood sample, nasopharyngeal aspirates, tears, spinal fluid, and middle ear aspirates.

In other embodiments, other markers for viral infection and/or bacterial infection may be used. For example, approximately 12% of host genes alter their expression after Lymphocytic Choriomeningitis Virus (LCMV) infection, and a subset of these genes can discriminate between virulent and nonvirulent LCMV infection. Major transcription changes have been given preliminary confirmation by quantitative PCR and protein studies and are potentially valuable candidates as biomarkers for arenavirus disease. Other markers for bacterial infection include, but are not limited to, procalcitonin, urinary trypsin inhibitor (uTi), lipopolysaccharide, IL-1, IL-6, IL-8, IL-10, ESR and an elevated WBC count (increased bands), Lactate, Troponin, vascular endothelial growth factor, platelet derived growth factor, cortisol, proadrenomedullin, macrophage migratory inhibitory marker, activated protein C, CD 4, 8, 13, 14, or 64, caspase, placenta derived growth factor, calcitonin gene-related peptide, high mobility group 1, copeptin, naturietic peptides, lipopolysaccharide binding protein, tumor necrosis factor alpha, circulating endothelial progenitor cells, complement 3a, and triggering receptor expressed on myeloid cells (trem-1).

In one embodiment, the infections being distinguished are respiratory infections. In other embodiments, other types of infections, which can be bacterial or viral, are differentiated using the system of the present invention. Some examples include, but are not limited to, encephalitis, meningitis, gastroenteritis, febrile respiratory illness (including bronchitis, pharyngitis, pneumonia), sinusitis, otitis media, urinary tract infections, and conjunctivitis.

EXAMPLE

One or more lysis agents are dried onto the sample application zone of a lateral flow strip. On a per strip basis, the lysis agent is made of approximately 2 microliters of 100 mM HEPES buffer (pH 8.0) containing 5% CHAPS and 2% NP-40 with 150 mM Sodium Chloride, 0.1% BSA, and 0.1% Sodium Azide (all percentages weight/volume). Up to 10 microliters of whole blood are then added to the sample application zone to be lysed in situ. MxA protein is released from inside white blood cells to react with an MxA monoclonal antibody on a visual tag (colloidal gold or visible latex beads). This complex traverses with a running buffer containing Triton X-100 and is captured by MxA monoclonal antibodies immobilized at the test line of the nitrocellulose membrane. This binding at the test line gives rise to a visible indication.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A method for detecting at least one target in a sample, comprising the steps of:
    a) transferring a sample that is not lysed onto a sample application zone of a sample analysis device;
    b) applying an elution medium comprising at least one first lysis agent to the sample analysis device to transfer the sample from the sample application zone to a detection zone, wherein the sample encounters the at least one first lysis agent in the elution medium such that the sample is lysed prior to reaching the detection zone; and
    c) analyzing the sample for a presence of the target in the sample, comprising the substep of detecting a presence of the target in the sample by detecting a signal from the labeled binding partner in the detection zone;
    wherein the sample application zone, and the detection zone are on a chromatographic test strip, and the chromatographic test strip further comprises a conjugate zone, wherein the conjugate zone comprises at least one labeled binding partner that is able to migrate with the elution medium and wherein the labeled binding partner encounters the sample while the sample is being transferred from the sample application zone to the detection zone and binds to the target when the target is present in the sample;
    wherein the chromatographic test strip further comprises a lysis zone that comprises at least one second lysis agent, wherein the lysis zone is located on the chromatographic test strip in a location selected from the group consisting of:
        i) between the sample application zone and the conjugate zone;
        ii) a location where at least a portion of the lysis zone overlaps the sample application zone;
        iii) a location where at least a portion of the lysis zone overlaps the conjugate zone; and
        iv) a location where at least a portion of the lysis zone overlaps the sample application zone and at least a portion of the lysis zone overlaps the conjugate zone.

2. The method of claim 1, further comprising the step of:
    d) determining at least one result of an analysis performed in step (c) within 20 minutes of transferring the sample in step (a).

3. The method of claim 2, wherein the result is determined within 10 minutes of transferring the sample in step (a).

4. The method of claim 2, wherein the result is determined within one to five minutes of applying the elution medium in step (b).

5. The method of claim 1, wherein the target is a target selected from the group consisting of pathogens and/or allergy-associated components; and wherein the sample is from a body fluid.

6. The method of claim 1, wherein the conjugate zone is located between the sample application zone and the detection zone.

7. The method of claim 1, wherein the chromatographic test strip further comprises a blocking zone comprising a barrier that slows or arrests lysed materials effectively larger than a porosity of the barrier.

8. The method of claim 7, wherein the barrier is selected from the group consisting of a physical barrier or a biological barrier.

9. The method of claim 7, wherein the blocking zone is located in a location on the chromatographic test strip selected from the group consisting of:
   a) between the sample application zone and the conjugate zone;
   b) between the conjugate zone and the detection zone; and
   c) between the sample application zone and the detection zone.

10. The method of claim 1, wherein the first lysis agent and the second lysis agent are selected from the group consisting of:
   a) at least one salt;
   b) at least one amphoteric agent;
   c) at least one ionic detergent;
   d) at least one non-ionic detergent;
   e) at least one enzyme;
   f) urea; and
   g) any combination of a) through f).

* * * * *